(12) United States Patent
Kong et al.

(10) Patent No.: US 6,245,545 B1
(45) Date of Patent: Jun. 12, 2001

(54) METHOD FOR CLONING AND PRODUCING THE SWAI RESTRICTION ENDONUCLEASE

(75) Inventors: Huimin Kong, Wenham; Lauren S. Higgins, Essex; Michael A. Dalton, Manchester, all of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/299,378

(22) Filed: Apr. 27, 1999

(51) Int. Cl.[7] ............................... C12N 9/22; C12N 9/10; C12N 1/21; C12N 15/52; C07H 21/04
(52) U.S. Cl. ..................... 435/199; 435/193; 435/252.3; 435/252.33; 435/320.1; 536/23.2
(58) Field of Search ................ 435/252.3, 252.33, 435/199, 193, 320.1; 536/23.2, 23.7

(56) References Cited

U.S. PATENT DOCUMENTS

| | | | |
|---|---|---|---|
| 5,158,878 | * 10/1992 | Prinz et al. | 435/91.53 |
| 5,175,101 | * 12/1992 | Gotz et al. | 435/6 |
| 5,200,333 | 4/1993 | Wilson | 435/6 |
| 5,320,957 | 6/1994 | Brooks et al. | 435/475 |
| 5,492,823 | 2/1996 | Xu | 435/199 |

OTHER PUBLICATIONS

Roberts, et al., Nucleic Acids Res. 26:338–350 (1998).
Kosykh, et al., Molec. Gen. Genet. 178:717–719 (1980).
Mann, et al., Gene 3:97–112 (1978).
Walder, et al., Proc. Nat. Acad. Sci. 78:1503–1507 (1981).
Bougueleret, et al., Nucl. Acid Re. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriol. 164:501–509 (1985).
Kiss, et al., Nucl. Acid Res. 13:6403–6421 (1985).
Szomolanyi, et al., Gene, 10:219–225 (1980).
Janulaitis, et al. Gene 20:197–204 (1982).
Kiss and Baldauf, Gene 21:111–119 (1983).
Walder, et al., J. Biol. Chem. 258:1235–1241 (1983).
Piekarowicz, et al. Nucl. Acid Res. 19:1831–1835 (1991).
Piekarowicz, et al., J. Bacteriology, 173:150–155 (1991).
Fomenkov, et al., Nucl. Acids Re. 22:2399–2403 (1994).
Lunnen, et al., Gene 74:25–32 (1988).
Raleigh and Wilson, Proc. Natl. Acad. Sci. USA 83:9070–9074 (1986).
Heitman and Model, J. Bact. 196:3243–3250 (1987).
Raleigh, et al., Genetics 122:279–296 (1989).
Waite–Rees, et al., J. Bacteriology, 173:5207–5219 (1991).
Ochman, et al., Genetics, 120:621 (1988).
Triglia, et al., Nucl. Acid Res. 16:8186 (1988).
Silver and Keerikatte, J. Cell. Biochem. (Suppl) 13E:306, Abstract No. WH239 (1989).

* cited by examiner

*Primary Examiner*—Elizabeth Slobodyansky
(74) *Attorney, Agent, or Firm*—Gregory D. Williams; James Gregory Cullem

(57) ABSTRACT

The present invention relates to the recombinant DNA which encodes the SwaI restriction endonuclease, modification methylase, and the production of SwaI restriction endonuclease from the recombinant DNA. Related expression vectors, pHKUV5 which features a strong, constitutive UV5 promoter without the Lac repressor binding site and pHKT7 which contains a powerful controllable T7 promoter and a low copy number origin of replication, are also disclosed.

4 Claims, 6 Drawing Sheets

FIG. 2

```
         10                  30                  50
ATGAACTTTAAAAAATACGAAGAAAATCTAGTAGCATCTATTGAAGAAGTTATTCAACGC
MetAsnPheLysLysTyrGluGluAsnLeuValAlaSerIleGluGluValIleGlnArg 70                  90                 110
ATTATAGATGATAAACATAGACCTAATATTATAGGTAAAACAAGAGTAGGCGCTGAAGTT
IleIleAspAspLysHisArgProAsnIleIleGlyLysThrArgValGlyAlaGluVal 130                 150                 170
AGCGATTACTTAGAAGATGAATTTGTAAAGTATATATCTAGTGGAAAGAGTAGTAGCTTA
SerAspTyrLeuGluAspGluPheValLysTyrIleSerSerGlyLysSerSerSerLeu 190                 210                 230
TATGATGCTCAAGGAGCACCTAAAGAAAAGACTAAAAACCCATGGGACGCAAGATGTAAA
TyrAspAlaGlnGlyAlaProLysGluLysThrLysAsnProTrpAspAlaArgCysLys 250                 270                 290
TTTAAGTTTATGGATAGAGAAGAAGAAATTTGGATTGATTTTAAAGCATTTAAAATAACT
PheLysPheMetAspArgGluGluGluIleTrpIleAspPheLysAlaPheLysIleThr 310                 330                 350
AACATGGATAGTAATCCGGATATTGGAACTCCTAATAAAATAGTTAAGTTCATTCATGAA
AsnMetAspSerAsnProAspIleGlyThrProAsnLysIleValLysPheIleHisGlu 370                 390                 410
GGGAATTTTTATTTAGTTTTTGTACTTGTGTATTATGAAAGTAAACAAGATGGTGTTGAA
GlyAsnPheTyrLeuValPheValLeuValTyrTyrGluSerLysGlnAspGlyValGlu 430                 450                 470
TTTGTAAAATATAATAATGATTATAAAAAAGTTTACTTATTAAAAGATGTTAATGAATCA
PheValLysTyrAsnAsnAspTyrLysLysValTyrLeuLeuLysAspValAsnGluSer 490                 510                 530
TTTAGAATTAATCCAAAACCACAGATGCAAGTTAATATTGCAGCAGAACCCACATTTAGA
PheArgIleAsnProLysProGlnMetGlnValAsnIleAlaAlaGluProThrPheArg 550                 570                 590
ACTAGAGAAGAATTTATTCATTTCTTTGTTAAAAAATGGAAAGAGTCATTTGAAAGACAG
ThrArgGluGluPheIleHisPhePheValLysLysTrpLysGluSerPheGluArgGln 610                 630                 650
ATAAAATCTTTAGAAAAAAAAGAAATAATGTTAAAAGATCTAGAAGATAAATTGAAAAAT
IleLysSerLeuGluLysLysGluIleMetLeuLysAspLeuGluAspLysLeuLysAsn

670
TCTAATGACAACTCAATTTAA
SerAsnAspAsnSerIleEnd
```

FIG. 3A

```
        10                    30                    50
ATGAAAAATTATAATTTAATAGACTTATATTCATTATATTTCGAAATTGACAAAGTAAAA
MetLysAsnTyrAsnLeuIleAspLeuTyrSerLeuTyrPheGluIleAspLysValLys 70                    90                   110
CTAAGAGATATGTTTCAGAATATATCAATTGAAGTAAAACTTAATGAGGCTCAAGTTGAT
LeuArgAspMetPheGlnAsnIleSerIleGluValLysLeuAsnGluAlaGlnValAsp 130                   150                   170
GAAATACTCAAACTAGATATATTTACATTTTATAATGAAATCAATCTATTAATAAGCAAA
GluIleLeuLysLeuAspIlePheThrPheTyrAsnGluIleAsnLeuLeuIleSerLys 190                   210                   230
ACAATTGAGACTTCTAATAGAAAAGATAATGGAATATATTTCACTCAAGATTTTAATGTT
ThrIleGluThrSerAsnArgLysAspAsnGlyIleTyrPheThrGlnAspPheAsnVal 250                   270                   290
ATAAAAAGGATAATACAATTATCTATTGATAAAATACCTAATACTTTATTAACAAAGAAA
IleLysArgIleIleGlnLeuSerIleAspLysIleProAsnThrLeuLeuThrLysLys 310                   330                   350
AAAGTATTAGATCCAGCTTGTGGTACGGGTATATTTTCAATAGCTTTCATACATGAAATT
LysValLeuAspProAlaCysGlyThrGlyIlePheSerIleAlaPheIleHisGluIle 370                   390                   410
TTCAACAGACAAATTAGTAAAAATTCTATAGTTGATTTTATAAATAACTACTTAGTAAAT
PheAsnArgGlnIleSerLysAsnSerIleValAspPheIleAsnAsnTyrLeuValAsn 430                   450                   470
ATAGATGTTTCAAATGAAATGATTAATTTTACTAAGATCAATATTCTTACTATGATGTAT
IleAspValSerAsnGluMetIleAsnPheThrLysIleAsnIleLeuThrMetMetTyr 490                   510                   530
TATCTATATAATGACATAAGTATCTTTGATAAAGTAAAACCTAATATATATGCTATAGAT
TyrLeuTyrAsnAspIleSerIlePheAspLysValLysProAsnIleTyrAlaIleAsp 550                   570                   590
TTTGTTTATCAAGAAAAACACAAAGAATTTAATTTATTTAATTATTTTAATTCTCAAAAT
PheValTyrGlnGluLysHisLysGluPheAsnLeuPheAsnTyrPheAsnSerGlnAsn 610                   630                   650
CAAAATTTTATTAATGATAATTTTGAGAATTTTGATATAGTTATAGGCAATCCTCCATAC
GlnAsnPheIleAsnAspAsnPheGluAsnPheAspIleValIleGlyAsnProProTyr 670                   690                   710
GTATCCTTGTATGGAAGACGAGCCATAAATAAGAGTGAAGATAAAAGACAATTTTTAATA
ValSerLeuTyrGlyArgArgAlaIleAsnLysSerGluAspLysArgGlnPheLeuIle 730                   750                   770
```

FIG. 3B

```
CGAAATTATGATTTTATACCTAAAAACGTAAAAAATGGAAAATTTAATTACACAATGTTT
ArgAsnTyrAspPheIleProLysAsnValLysAsnGlyLysPheAsnTyrThrMetPhe 790            810             830
TTTATTGAAAATGGTTTACAACTACTAAAAAAGAATGGTACTTTAACATTTATTGTAGAT
PheIleGluAsnGlyLeuGlnLeuLeuLysLysAsnGlyThrLeuThrPheIleValAsp 850            870             890
ATAACTTTACTTGAAAGTTCTTTTGAATCAATTAGAAAATATATTTTAGAAACTGCCATT
IleThrLeuLeuGluSerSerPheGluSerIleArgLysTyrIleLeuGluThrAlaIle 910            930             950
ATAAAGCAACTTGATATCAATTTAAAAGCTTTTAGTGATGTAGTTAGTGGACAAATAATC
IleLysGlnLeuAspIleAsnLeuLysAlaPheSerAspValValSerGlyGlnIleIle 970            990            1010
ATTTCTCTTTTAAAAAAATGCATCCAACAAAGAAGCTATTGTAAGTATCAAAGATTGGCAA
IleSerLeuLeuLysAsnAlaSerAsnLysGluAlaIleValSerIleLysAspTrpGln 1030           1050            1070
AATAATAACACAATTCAAATTAATCAAGATATATGGTTGCATGATAAATTTTATCGTTTT
AsnAsnAsnThrIleGlnIleAsnGlnAspIleTrpLeuHisAspLysPheTyrArgPhe 1090           1110            1130
AATATTAGCGATAAGAAAATAAATTCAATTTTAGAGAAAGTTTACAATAAATCAGATGAA
AsnIleSerAspLysLysIleAsnSerIleLeuGluLysValTyrAsnLysSerAspGlu 1150           1170            1190
CTTCAATATTATTTTCCTAAGAAAGAGTTACGTACTTCTACTATGTTATTGAATATGGAA
LeuGlnTyrTyrPheProLysLysGluLeuArgThrSerThrMetLeuLeuAsnMetGlu 1210           1230            1250
TCTTCCTTCGTTAAAGATTATAAACCAGAAACGGATTTTCACGTAATGCCTTATTATAAG
SerSerPheValLysAspTyrLysProGluThrAspPheHisValMetProTyrTyrLys 1270           1290            1310
GGAGCCAAAAAATTTATCTTTTCCATTTCAAAATATGCATTCAAATCACTATTTTATATAC
GlyAlaLysAsnLeuSerPheProPheGlnAsnMetHisSerAsnHisTyrPheIleTyr 1330           1350            1370
GATACAGCTTTACAAAAAAAGATTAATGATTCACTTCATGAAGAATTATTAAAAAAAGGA
AspThrAlaLeuGlnLysLysIleAsnAspSerLeuHisGluGluLeuLeuLysLysGly 1390           1410            1430
ATAAAAAATAAAAAAAGAATTGGTTTAGGTAACTTAGAGGTGTTTAAAAACCCGAAACTT
IleLysAsnLysLysArgIleGlyLeuGlyAsnLeuGluValPheLysAsnProLysLeu 1450           1470            1490
TTTATTAGACAATCTGCTAATAAGCTTATAGCAACCTTTGATGGTAAAATGTCAGCTTCA
PheIleArgGlnSerAlaAsnLysLeuIleAlaThrPheAspGlyLysMetSerAlaSer
```

FIG. 3C

```
          1510                1530                1550
AATAATAGTTTATATATCTTAAGTAAAGCAACTAACGATATAAAAGATATAAATATGCTA
AsnAsnSerLeuTyrIleLeuSerLysAlaThrAsnAspIleLysAspIleAsnMetLeu 1570                1590                1610
AAAATTACATGTGCTCAACTAAATTCTGAATTATTAACATTTATTGCACTTACAAATAGA
LysIleThrCysAlaGlnLeuAsnSerGluLeuLeuThrPheIleAlaLeuThrAsnArg 1630                1650                1670
ATTATCCGAAAAGCTGAAGGCAAACAACCTCAAATTAAATTGTCAGATTTAAAAACAATT
IleIleArgLysAlaGluGlyLysGlnProGlnIleLysLeuSerAspLeuLysThrIle 1690                1710                1730
CCACTATGTTTTAATGAAGAGATTAATTCTAAGTTATTAATTTTTGCAGAAAATGCTACT
ProLeuCysPheAsnGluGluIleAsnSerLysLeuLeuIlePheAlaGluAsnAlaThr 1750                1770                1790
AAAAAAAATAATGAATTAGAAAGTTCTTTAGAAAAAATCAATCAAATTATTTATAAATAT
LysLysAsnAsnGluLeuGluSerSerLeuGluLysIleAsnGlnIleIleTyrLysTyr 1810                1830                1850
TATGATATTAACGGTGAAGAAGTAGAATTTATTAAAAACTATATTAATTCAAATTAG
TyrAspIleAsnGlyGluGluValGluPheIleLysAsnTyrIleAsnSerAsnEnd
```

METHOD FOR CLONING AND PRODUCING THE SWAI RESTRICTION ENDONUCLEASE

BACKGROUND OF THE INVENTION

The present invention relates to the recombinant DNA which encodes the SwaI restriction endonuclease and modification methylase, and the production of SwaI restriction endonuclease from the recombinant DNA. SwaI restriction endonuclease (see U.S. Pat. No. 5,158,878) is originally isolated from *Staphlococcus warneri*. It recognizes the DNA sequence 5' ATTTAAAT 3' and cleaves the phosphodiester bond 5' to the second A of the recognition sequence to produce a blunt end.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Type II restriction endonucleases act by recognizing and binding to particular sequences of nucleotides (the 'recognition sequence') along the DNA molecule. Once bound, they cleave the DNA molecule at specific positions. Different restriction endonucleases have affinity for different recognition sequences. More than 3000 restriction endonucleases have been characterized so far, and they recognize 212 different recognition sequences (Roberts, R. J., Macelis, D. Nucleic Acids Res. 26:338–350 (1998)).

It is thought that in nature, restriction endonucleases play a protective role in the welfare of the bacterial cell. They enable bacteria to resist infection by foreign DNA molecules like bacteriophages and plasmids that would otherwise destroy or parasitize them. They impart resistance by cleaving invading foreign DNA molecules each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify the target nucleotide within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiable foreign DNA, that is sensitive to restriction endonuclease recognition and cleavage.

With the advent of genetic engineering technology, it is now possible to clone genes and to produce the proteins that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., Molec. Gen. Genet 178: 717–719, (1980); HhaII: Mann et al., Gene 3: 97–112, (1978); PstI: Walder et al., Proc. Nat. Acad. Sci. 78 1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985)).

A third approach which is being used to clone a growing number of systems, involves selection for an active methylase gene (see, e.g., U.S. Pat. No. 5,200,333 and BsuRI: Kiss et al., Nucl. Acid. Res. 13: 6403–6421, (1985)). Since restriction and modification genes are often closely linked, both genes can often be cloned simultaneously. This selection does not always yield a complete restriction system however, but instead yields only the methylase gene (BspRI: Szomolanyi et al., Gene 10: 219–225, (1980); BcnI: Janulaitis et al, Gene 20: 197–204 (1982); BsuRI: Kiss and Baldauf, Gene 21: 111–119, (1983); and MspI: Walder et al., J. Biol. Chem. 258: 1235–1241, (1983)).

Another method for cloning methylase and endonuclease genes is based on a colorimetric assay for DNA damage (see, U.S. Pat. No. 5,492,823). When screening for a methylase, the plasmid library is transformed into the host *E. coli* strain such as AP1-200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et. al., Nucleic Acids Res. 19:1831–1835, (1991) and Piekarowicz, et. al. J. Bacteriology 173:150–155 (1991),). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et. al. Nucleic Acids Res. 22:2399–2403 (1994)).

Sometimes the straight-forward methylase selection method fails to yield a methylase (and/or endonuclease) clone due to various obstacles. See, e.g., Lunnen, et al., Gene, 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see, U.S. Pat. No. 5,320, 957).

Another obstacle to cloning restriction-modification systems lies in the discovery that some strains of E. coli react adversely to cytosine or adenine modification; they possess systems that destroy DNA containing methylated cytosine (Raleigh and Wilson, Proc. Natl. Acad. Sci., USA 83:9070–9074, (1986)) or methylated adenine (Heitman and Model, J. Bact. 196:3243–3250, (1987); Raleigh, Trimarchi, and Revel, Genetics, 122:279–296, (1989) Waite-Rees, et al., J. Bacteriology, 173:5207–5219 (1991)). Cytosine-specific or adenine-specific methylase genes cannot be cloned easily into these strains, either on their own, or together with their corresponding endonuclease genes. To avoid this problem it is necessary to use mutant strains of E. coli (McrA- and McrB- or Mrr-) in which these systems are defective.

A third potential difficulty is that some restriction endonuclease and methylase genes may not express in E. coli due to differences in the transcription machinery of the source organism and E. coli, such as differences in promoter and ribosome binding sites. The methylase selection technique requires that the methylase express well enough in E. coli to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

A unique combination of methods was used to directly clone the SwaI endonuclease gene and express the gene in an E. coli strain premodified by SwaI methylase. To clone the SwaI endonuclease gene directly, the N-terminal amino acid sequence of highly purified native SwaI restriction endonuclease was determined. Degenerate primers were designed based on the N-terminal amino acid sequence and PCR techniques were used to amplify the DNA fragment that encodes the amino termini of the SwaI endonuclease protein. The PCR product was sequenced and the information was used to design primers for inverse PCR reactions. By chromosome walking via inverse PCR, the endonuclease open reading frame, swaIR, was deduced. Continuing with inverse PCR, an open reading frame was found adjacent to the endonuclease gene. Blast analysis suggested that this gene encoded an adenine methylase (draIIIM).

A new expression vector, pHKUV5, was specially engineered to express SwaI methylase. SwaI endonuclease gene was cloned into a low copy-number T7 expression vector, pHKT7, and transformed into the E. coli host which was premodified by SwaI methylase cloned in pHKUV5. This recombinant E. coli strain (NEB#1183) produces about $2.0 \times 10^5$ units SwaI endonuclease per gram cell. The yield of recombinant SwaI endonuclease is 10-fold higher than the yield of native endonuclease from Staphylococcus warneri.

BRIEF DESCRIPTION OF THE DRAWINGS

FIG. 2 shows the DNA sequence of swaIR gene (SEQ ID NO:1) and its encoded amino acid sequence (SEQ ID NO:2).

FIG. 3 shows the DNA sequence of swaIM gene (SEQ ID NO:3) and its encoded amino acid sequence (SEQ ID NO:4).

DETAILED DESCRIPTION OF THE INVENTION

The cloning of the SwaI restriction endonuclease gene from Staphylococcus warneri proved to be challenging. A methylase selection strategy was tried but no methylase expression clones were isolated. The method described herein by which the SwaI restriction endonuclease is preferably cloned and expressed in the E. coli utilizes the following steps:

1. Purification of the SwaI restriction endonuclease to near homogeneity and N-terminal amino acid sequence determination.

Four chromatography columns were used to purify the SwaI endonuclease protein. They included a Heparin Hyper-D column, a Source™-15Q column, a Source™-15S and a Heparin TSK-Guardgel column. The purification yielded two protein bands at approximately 63 kDa and 28 kDa on an SDS-PAGE protein gel following Coomassie blue staining. For both proteins, the N-terminal amino acid residues were determined by sequential degradation of the purified protein on an automated sequencer. The N-terminal amino acid sequence was the same for both proteins.

2. Amplification of 5' region of SwaI endonuclease gene and subsequent cloning into plasmid.

Degenerate primers were designed based on the N-terminal amino acid sequence and these primers were used to PCR amplify the 5' end of the endonuclease gene. PCR products were cloned into plasmid pCAB16 and sequenced. The 99-bp PCR fragment which corresponded to the 5' end of the SwaI endonuclease gene was then identified by comparing the amino acid sequences deduced from the cloned DNA with the N-terminal amino acid sequence of the SwaI endonuclease protein.

3. Chromosome walking via inverse PCR to isolate the SwaI endonuclease and methylase genes.

Figure 1:
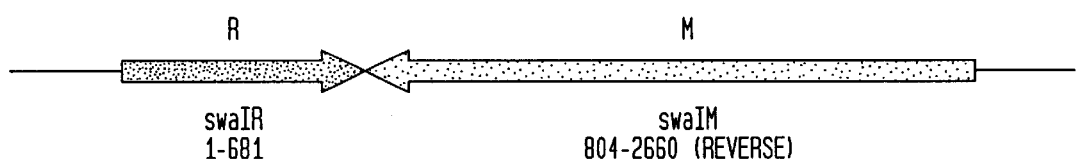
FIG. 1 shows the gene organization of SwaI restriction-modification system. swaIR: SwaI endonuclease gene; swaIM: SwaI methylase gene.

To clone the entire SwaI endonuclease gene as well as its corresponding DNA methylase gene, inverse PCR techniques were adopted to amplify DNA adjacent to the original 99-bp endonuclease gene fragment (Ochman, et al., Genetics, 120:621 (1988), Triglia, et al., Nucl. Acids Res., 16:8186 (1988) and Silver and Keerikatte, J. Cell. Biochem., (Suppl.) 13E:306, Abstract No. WH239 (1989)) and the amplified products were sequenced. In total, four rounds of inverse PCR were performed. At that point, two open reading frames (ORF) were identified (FIG. 1). The 681-bp endonuclease gene (swaIR) encodes a 227-amino acid protein with a deduced molecular weight of 26,842, which agrees with the observed molecular mass of SwaI endonuclease. A 1857-bp ORF, swaIM, is found adjacent to the swaIR gene, oriented in a convergent manner. The protein sequence deduced from swaIM gene shares significant sequence similarity with other adenine methylases.

4. Expression of SwaI endonuclease gene using pHKUV5 and pHKT7 plasmids.

The two-step method for cloning restriction-modification systems is described in U.S. Pat. No. 5,320,957. The first step includes introducing the methylase gene into a host cell and expressing the gene therein to protect the host cell from corresponding endonuclease digestion by pre-modification of recognition sequences. The second step includes introduction of the endonuclease gene into the pre-modified host cell and subsequent endonuclease production.

Figure 4:
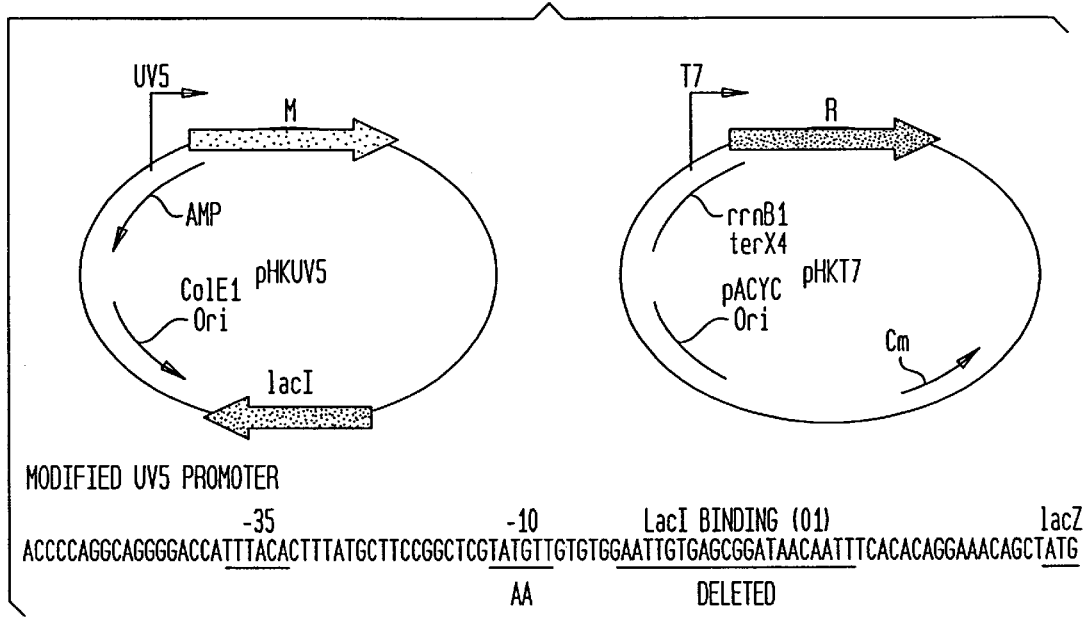
FIG. 4 shows two expression vectors, pHKUV5 and pHKT7.

A new plasmid, pHKUV5, was used to express the swaIM gene. pHKUV5 features a strong, constitutive UV5 promoter ($P_{uv5}$) without the Lac repressor (LacI) binding site, so that the methyltransferase gene will be expressed continuously at high levels (FIG. 4). In addition, pHKUV5 also carries a high copy number origin of replication (ColE1), and LacI gene. Because LacI gene is on a high copy number plasmid, it is highly expressed. However, the large amount of LacI won't interfere the expression of the methylase gene from $P_{uv5}$, because the LacI binding site has been deleted from the promoter.

Plasmid pHKUV5 was engineered from plasmid pUC19 (New England Biolabs, #304). First, synthetic oligonucleotides were used to convert $P_{lac}$ of pUC19 into a stronger UV5 promoter by changing the −10 sequence of $P_{lac}$ from TATGTT to more conserved TATAAT (FIG. 4). At that time, the LacI binding site was deleted. Next, the LacI gene was cloned from a donor plasmid into pHKUV5. The swaIM gene was then cloned into plasmid pHKUV5 and transformed into E. coli cells. The host cells were then fully modified by the pHKUV5-swaIM construct.

To express the SwaI endonuclease gene, low copy number vector pHKT7 was used (FIG. 4). Plasmid pHKT7 contains an inducible T7 promoter which is controlled by LacI. The origin of replication is from plasmid p15A which is compatible with the pHKUV5 plasmid. The basal level of gene expression is extremely low for genes cloned into pHKT7 for two reasons. First, because the T7 promoter is on a low copy number plasmid, expression is reduced. Secondly, high levels of LacI repressor made from the high copy number plasmid pHKUV5 also act to keep expression levels low.

The endonuclease gene, swaIR, was cloned into pHKT7, and then introduced into E. coli ER2566 containing pHKUV5-swaIM. The culture was grown to middle log and then induced by the addition of IPTG to a final concentration of 0.4 mM. The yield of recombinant SwaI endonuclease is $2.0 \times 10^5$ units per gram cells which is 10-fold higher than the yield of native endonuclease from Staphylococcus warneri.

The following Example is given to additionally illustrate embodiments of the present invention as it is presently preferred to practice. It will be understood that this Example is illustrative, and that the invention is not to be considered as restricted thereto except as indicated in the appended claims.

The references cited above and below are herein incorporated by reference.

EXAMPLE 1

Purification of the SwaI Endonuclease and Determination of its Protein Sequence

1. Purification of the SwaI restriction endonuclease from Staphylococcus warneri to near homogeneity:

Staphylococcus warneri cells were propagated at 30° C. The cells were harvested by centrifugation after 20 hours of growth and stored at −70° C. until used. 451 g of cells were thawed at 4° C. overnight and then resuspended in 1.5 L of Buffer A (20 mM KPO4, 10 mM BME, 0.1 mM EDTA, 5% glycerol, pH 6.9) supplemented with 50 mM NaCl and 120 mg lysostafin (Sigma, St. Louis, Mo.). The resuspended cells were incubated on a stir plate at room temperature. After an eight hour incubation, 25 ml of protease inhibitor cocktail (P8465; Sigma, St. Louis, Mo.) was added and the stir plate apparatus along with the cells were moved into a refridgerator and the cells were stirred overnight at 4° C. The following morning the cells were incubated at room temperature for two hours. The cells were then sonicated until approximately 3.1% of the total cell protein was released and then the cells were broken with a Manton-Gaulin homogenizer. The extract was centrifuged at 14,000 rpm for 10 minutes at 4° C.

All of the following procedures were performed on ice or at 4° C. The supernatant was loaded onto a 400 ml XK50/30 Heparin Hyper-D column (BioSepra Inc., Marlborough, Mass.) equilibrated with buffer A.1 (50 mM NaCl, 20 mM KPO$_4$, pH 7.0, 0.1 mM EDTA, 10 mM beta-mercaptoethanol and 5% glycerol). The column was washed with 800 ml of buffer A.1, followed by a 4 L linear gradient from 50 mM NaCl to 1 M NaCl in buffer A (20 mM KPO4, PH 7.0, 0.1 mM EDTA, 10 mM beta-mercaptoethanol and 5% glycerol). 25 ml fractions were collected. Fractions were assayed for SwaI restriction activity with M13mp19RF DNA and the peak of restriction enzyme activity was found to elute from the column between 0.62 to 0.71 M NaCl and was pooled. The amount of SwaI endonuclease was estimated to be $11.0 \times 10^6$ units.

This Heparin Hyper-D pool was dialyzed against 8 L of 100 mM NaCl in buffer B (20 mM Tris-HCl, pH 8.0, 0.1 mM EDTA, 10 mM beta-mercaptoethanol and 5% glycerol, final pH of 7.8). The dialyzed pool was diluted with buffer B to a final concentration of 50 mM NaCl and applied to a 90 ml Source™-15Q column (Pharmacia Biotech, Piscataway, N.J.) equilibrated in buffer B.1 (50 mM NaCl, 20 mM Tris-HCl, pH 8.0, 0.1 mM EDTA, 10 mM beta-mercaptoethanol and 5% glycerol, final pH of 7.8). The column was washed with 200 ml of buffer B1 followed by a 1 L linear gradient of 50 mM NaCl to 700 mM NaCl in buffer B. 10 ml fractions were collected. Fractions were assayed for SwaI activity with M13mp19RF DNA. The majority of restriction enzyme activity flowed through the column ($8.6 \times 10^6$ units). Approximately 960,000 units bound to the column and were eluted in the first 15 fractions.

The first fifteen fractions were pooled and diluted with 0.5 volumes of buffer A and loaded onto a 8 ml HR 10/10 Source™-15S FPLC column (Pharmacia Biotech, Piscataway, N.J.) that had been equilibrated with Buffer A.1. The column was washed with 10 ml of buffer A.1 and then a 90 ml linear gradient from 50 mM NaCl to 800 mM NaCl in Buffer A was performed. 1.5 ml fractions were collected. Fractions were assayed for SwaI activity with M13mp19RF DNA. A very small amount of activity flowed through the column and more than 544,000 units were eluted in fractions 17–19.

Fractions 17–19 were combined and diluted to 50 mM NaCl in buffer B. The diluted pool was then loaded onto a 9 ml HR 10/10 Heparin 5PW TSK Guardgel column (Toso Haas) that had been previously equilibrated with buffer B1. The column was washed with 10 ml buffer B1 followed by a 100 ml linear gradient from 50 mM NaCl to 1 M NaCl in buffer B. 1.5 ml fractions were collected. Fractions were assayed for SwaI activity with M13mp19RF DNA. The peak of the enzyme activity eluted at 0.56 M NaCl. Greater than 200,000 units of SwaI activity were purified to near homogeneity. 20 uL of the peak fractions (46 and 47) were loaded onto an SDS-PAGE protein gel and subjected to electrophoresis. The gel was stained with Coomassie blue R-250 and two prominent bands at approximately 63 kDa and 28 kDa corresponding to the SwaI restriction endonuclease activity were observed.

2. Determining the N-terminal protein sequence of SwaI endonuclease

The SwaI restriction endonuclease, prepared as described was subjected to electrophoresis and electroblotted according to the procedure of Matsudaira (Matsudaira, P., J. Biol. Chem. 262:10035–10038, (1987)), with modifications as previously described (Looney, M., et al. Gene 80:193–208, (1989)). The membrane was stained with Coomassie blue R-250 and the protein bands of approximately 63 kDa and 28 kDa were excised and subjected to sequential degradation on an Applied BioSystems Division, Perkin-Elmer Corporation (Foster City, Calif.) Model 407A gas phase protein sequencer (Waite-Rees, et al. J. Bacteriol. 173:5207–5219, (1991)). The first 31 residues of both kDa protein bands corresponded to M-N-F-K-K-Y-E-E-N-L-V-A-S-I-E-E-V-I-Q-X-I-I-D-D-K-X-X-P-N-I-I (SEQ ID NO:5).

EXAMPLE 2

Cloning of the SwaI Restriction-Modification Genes

1. Purification of genomic DNA from *Staphylococcus warneri*

To prepare the genomic DNA of *Staphylococcus warneri*, 10 g of cells were resuspended in 20 ml of 25% Sucrose, 50 mM Tris, pH 8.0 and mixed until the solution was homogenous. Ten ml of 0.25M EDTA, pH 8.0 plus 6 ml of freshly-prepared 10 mg/ml lysozyme in 0.25M Tris-HCl (pH 8.0) were added and the solution was incubated overnight at 4° C. Lysostafin was added to the cells and the mix was incubated at 37° C. for one hour. Twenty four ml of Lytic mix (1% Triton-X100, 50 mM Tris, 62 mM EDTA, pH 8.0) and 5 ml of 10% SDS were then added and the solution was gently mixed. The solution was extracted with one volume of equilibrated phenol/chloroform (50:50, v/v) and the aqueous phase was recovered. The aqueous solution was then dialyzed against four changes of 2 L of 10 mM Tris-HCl (pH 8.0), 1 mM EDTA. The dialyzed solution was digested with RNase A (100 µg/ml) at 37° C. for 1 hour. The DNA was precipitated by the addition of ¹⁄₁₀th volume 5 M NaCl and 0.55 volume of 2-propanol and spooled on a glass rod. The DNA was air dried and dissolved in 5 ml TE (10 mM Tris, 1 mM EDTA, pH 8.0) to a concentration of approximately 655 µg/ml and stored at 4° C.

2. Cloning the 5' region of the SwaI endonuclease gene into pCAB16 pCAB16 was digested with BsaAI by incubating the vector for 1 hour at 37° C. in the conditions described below.

120 µl pCAB 16 (6–12 µg)
10 µl BsaAI (50 U)
40 µl 10× NEB Buffer #3
230 µl dH₂O

The BsaAI in the reaction was heat killed by incubating for 15 minutes at 75° C. The vector was then dephosphorylated by incubating 100 µl (2 µg) of digested vector with 1 unit of shrimp alkaline phosphatase in 100 mM MgCl₂ for 1 hour at 37° C.

Degenerate primers were designed based on the following amino acid sequences derived from the SwaI N-terminal protein sequence: 1) N-F-K-K-Y-E-E (SEQ ID NO:6) and 2) I-I-G-K-T. They were designed to hybridize in a convergent manner with DNA around the 5' end of the SwaI endonuclease gene.

Primer 1 5' AAYTTYAARAARTAYGARGAG 3' (SEQ ID NO:7)
Primer 2 5' NGTYTTNCCDATDAT 3' (SEQ ID NO:8)

These primers were synthesized and each was kinased by incubating 10 µg of primer with 100 units of T4 Polynucleotide Kinase, 20 µl 10× T4 Polynucleotide Kinase Buffer, and 10 µl of 10 mM ATP, in a 200 µl reaction volume at 37° C. for 30 minutes. The kinase was heat inactivated by incubating the reaction at 65° C. for 10 min.

In the reaction that was successful in amplifying the product, a reaction mix was made by combining:

150 µl of Taq PCR Buffer (no magnesium)
15 µl of 20 mM dNTP solution
75 µl of kinased primer 1 (3.75 ug)
75 µl of kinased primer 2 (3.75 ug)
15 µl of 1 M MgCl₂
22.5 µl of purified bacterial DNA template (~15 ug)
1140 µl dH₂O
7 µl (35 units) of Taq DNA Polymerase The PCR amplification conditions were: 35 cycles of 94° C. for 30 seconds, 35° C. for 30 seconds and 72° C. for 20 seconds. 7.5 ul of Klenow (35 units, NEB#212) were added following PCR and the reaction was incubated at room temperature for 15 minutes followed by 75° C. for 20 minutes. The reaction was ethanol precipitated and the final DNA pellet was resuspended in 60 ul of dH₂O. The resuspended reaction was electrophoresed on a 3% low melting temperature agarose gel (NuSieve Agarose, FMC BioProducts, Rockland, Me.) in TAE buffer (40 mM Tris-Acetate, pH 8, 1 mM EDTA). The 99-bp DNA band was excised and the gel slice was incubated at 65° C. for 10 minutes. The temperature was then reduced to 40° C. Two ul of Beta-Agarase (2 units) was added and the incubation continued at 40° C. for an hour. A ligation was then performed by combining the following at 37° C.:

3 µl prepared pCAB16 (50 ng)
5 µl PCR product (50 ng)
2.5 µl 10× T4 DNA Ligase Buffer
1 µl Concentrated T4 DNA Ligase (2000 units)
13.5 µl dH₂O The reaction was incubated at 37° C. for one hour and then at 25° C. for one hour. It was then placed in an ice bucket filled with water and ice that sat in the refrigerator. The reaction was incubated as such overnight. Ten µl of the overnight ligation reaction was transformed into 100 µl of competent cells (cat.#L2011, Promega, Madison, Wis.) by combining the DNA and cells and incubating on ice for 10 minutes followed by 45 seconds at 42° C. The entire volume was plated on an Ampicillin LB plate and incubated overnight at 37° C. Colonies that grew were inspected for the correct plasmid construct by purifying the plasmid DNA using the Qiagen QIAprep Spin Plasmid Kit and digesting with AseI to see if the PCR product was cloned into the vector.

5 µl miniprep
1.5 µl 10× NEB #3
0.5 ul AseI
8 µl dH₂O

The above reaction was incubated at 37° C. for 30 minutes. Minipreps containing the correct size insert were sequenced. The DNA sequence was translated in six reading frames to check whether the deduced amino acid sequence corresponded with the N-terminal sequence of SwaI protein.

3. Chromosome walking via inverse PCR to isolate the SwaI endonuclease and methylase genes A) Prepare genomic DNA—Four templates were prepared for four consecutive inverse PCR reactions; Sau3AI, RsaI, BstyI and DraI. In the case of Sau3AI, 1.5 µg of bacterial DNA was digested with 100 units of Sau3AI restriction endonuclease in 1× Sau3AI buffer supplemented with BSA to a final concentration of 0.1 mg/ml in a 50 µl reaction volume. In the case of RsaI, 1.5 µg of bacterial DNA was digested with 50 units of RsaI restriction endonuclease in 1× NEB Buffer 1 in a 50 µl reaction volume. The BstyI template was prepared by digesting 1.5 µg of bacterial DNA with 50 units of BstyI restriction endonuclease in 1× BstyI buffer supplemented with BSA to a final concentration of 0.1 mg/ml in a 50 µl reaction volume. Finally, the DraI template was prepared by digesting 1.5 ug of bacterial DNA in 1× NEB buffer 4 with 100 units of DraI restriction endonuclease in a 50 ul reaction volume. All four reactions were incubated at optimum temperatures for one hour. The digests were confirmed by running 13 ul of the digestion reaction on a 1% agarose gel. The reactions were then heat killed by incubating at 70° C. for 20 minutes. Circularization was then achieved by incubating the remaining 37 µl (~1 µg) in 1× T4 DNA Ligase Buffer with 3000 units of T4 DNA Ligase in a 500 µl reaction volume at 16° C. overnight. A portion of this circularization ligation reaction was then used as the template for subsequent inverse PCR reactions.

B) Sau3AI inverse PCR—Inverse PCR primers were synthesized based on the DNA sequence of the piece of the SwaI endonuclease gene cloned into pCAB16:

5' TTCTTCAATAGATGCTACTAG 3' (194-24) (SEQ ID NO:9)

5' GTTATTCAACGCATTATAGA 3' (194-25) (SEQ ID NO:10)

Inverse PCR was carried out using primers 194-24 and 194-25 and the above mentioned Sau3AI DNA template. An approximately 850 base pair product was produced in the Sau3AI circular template PCR reaction. This product was gel purified and resuspended in 30 µl dH$_2$O. The PCR product was then sequenced using an ABI 373 automated sequencing system according to the manufacturer's instructions. The PCR primers above were used as the sequencing primers. The Sau3AI inverse PCR product contained approximately 640 bp of the SwaI ORF.

C. RsaI inverse PCR reaction—Two inverse PCR primers complementary to newly read endonuclease ORF sequence from the Sau3AI PCR product were then synthesized, as below, and used in an inverse PCR reaction. Template preparation, inverse PCR, purification and DNA sequencing were performed as above but the RsaI ligation was used to create the template as opposed to the Sau3AI ligation. A 1.1 Kb PCR product was generated and sequenced. The data revealed the remaining endonuclease ORF sequence and part of the swaIM DNA sequence.

5' CACATTTAGAACTAGAGAAGAA 3' (195-5) (SEQ ID NO:11)

5' GGTTCTGCTGCAATATTAACTTG 3' (195-6) (SEQ ID NO:12)

D. BstYI inverse PCR reaction—Two inverse PCR primers complementary to newly read sequence from the RsaI PCR product were then synthesized, as below, and used in an inverse PCR reaction. Template preparation, inverse PCR, purification and DNA sequencing were performed as above but the BstYI ligation was used in the inverse PCR template. A 1.7 Kb PCR product was generated and sequenced. The 858-bp of novel sequence revealed the more of the swaIM gene.

5' TAATCTTTAACGAAGGAAGATTCC 3' (196-39) (SEQ ID NO:13)

5' TAAACCAGAAACGGATTTTCAC 3' (196-40) (SEQ ID NO:14)

D. DraI inverse PCR reaction—Two inverse PCR primers complementary to newly read sequence from the BstyI PCR product were then synthesized, as below, and used in an inverse PCR reaction. Template preparation, inverse PCR, purification and DNA sequencing were performed as above but the DraI ligation was used in the inverse PCR reaction. A 2.0 Kb PCR product was generated and sequenced. The novel sequence revealed the rest of the swaIM gene.

5' GGTATAAAATCATAATTTCGTATTA 3' (196-178) (SEQ ID NO:15)

5' TAAAAACGTAAAAAATGGAAAA 3' (197-31) (SEQ ID NO:16)

EXAMPLE 3

Expression of the SwaI Restriction Endonuclease

1. Cloning the SwaI methylase on a compatible vector

The SwaI methylase gene (swaIM) was expressed by inserting the gene into an expression vector, pHKUV5, directly downstream of the strong UV5 promoter. To accomplish this, two oligonucleotide primers were synthesized utilizing the DNA sequence data. The forward oligonucleotide primer contained a PstI site to facilitate cloning, a stop codon in frame with the lacZ gene to terminate translation of the lacZ protein, a ribosome binding site (RBS) and 24 nucleotides complementary to *Staphylococcus warneri* DNA for hybridization:

5'-AAAACTGCAGATAAGGAGGTGATCGTATGAAAAATTATAATTTAATAGAC-3' (198-140) (SEQ ID NO:17)

The reverse primer was designed to hybridize to *Staphylococcus warneri* DNA at the 3' end of the SwaI gene. It contained a BamHI restriction site to facilitate cloning and a SwaI site which was used to test the in vivo SwaI methylase activity.

5' -CGCGGATCCATTTAAATCTAATTTGAATTAATATAGTTTTTA-3' (198-132) (SEQ ID NO:18)

These two primers were used to amplify the swaIM gene from Staphylococcus warneri genomic DNA by combining:

10 µl 10× Vent® ThermoPol Buffer

10 µl of 2 mM dNTPs 0.5 µl (300 ng) *Staphylococcus warneri* genomic DNA

1 µl primer 198-140 (75 ng)

1 µl primer 198-132 (75 ng)

75.5 µl dH$_2$O

1 µl (0.1 units) Deep Vent® polymerase

1 µl Taq DNA polymerase (5 units)

and amplifying for 25 cycles at 94° C. for 30 seconds, 50° C. for 1 minute and 72° C. for 2 minutes. The amplification product was purified using the Promega Wizard PCR Prep Kit. 500 ng of pHKUV5 vector and the remaining PCR product (~2 µg) were both digested with 20 units of BamHI and 20 units of PstI, supplemented with 0.1 mg/ml BSA in 1× NEB BamHI buffer in a 65 µl reaction that was incubated at 37° C. for one hour. The digests were run on a 1% low melting temperature NuSieve agarose gel in TAE buffer. The PCR and vector DNA bands were excised out and the gel slices were treated with Beta-Agarase for one hour at 40° C. The reactions were then frozen and thawed and the remaining solid gel pieces were quickly spun out using a microcentrifuge. The supernatant was ethanol precipitated and the final DNA pellets were resuspended in water. The DNA concentrations were determined by visual inspection on an agarose gel. The ligation of pHKUV5 and swaIM was performed by combining the following:

5 µl prepared pHKUV5 (100 ng)
5 µl methylase PCR product (500 ng)
5 µl 10× T4 DNA Ligase Buffer
2 µl T4 DNA Ligase (800 units)
33 µl dH$_2$O The reaction was incubated at 37° C. for one hour and ten µl of the ligation reaction was transformed into *E. coli* strain ER2566. Individual colonies were isolated and analyzed by digesting minipreps with the cloning enzymes to ensure that the methylase gene had indeed been cloned into the vector:

7 µl miniprep
1.5 µl 10× BamHI buffer
1.5 µl 1 mg/ml BSA
0.5 µl PstI (10 U)
0.5 µl BamHI (10 U)
4 µl dH$_2$O The digests were incubated at 37° C. for one hour.

The minipreps that were the correct construct were then digested with SwaI to check for methylase protection:

7 µl miniprep
1.5 µl 10× NEBuffer 3
1.5 µl 1 mg/ml BSA
1 µl SwaI (10 U)
4.5 µl dH$_2$O The digests were incubated at 25° C. for one hour. One µl of a clone that was resistant to SwaI digestion was transformed into ER2566 cells for the purpose of making calcium chloride competent cells.

2. Cloning and expression of the SwaI endonuclease gene

The SwaI endonuclease gene (swaIR) was expressed by inserting the gene into a expression vector, pHKT7, directly downstream of a strong inducible T7 promoter and a conserved ribosome binding site (RBS). To accomplish this, two oligonucleotide primers were synthesized utilizing the DNA sequence data. The forward oligonucleotide primer contained a BamHI site to facilitate cloning, an ATG start codon of the SwaI endonuclease gene and 24 nucleotides complementary to *Staphylococcus warneri* DNA for hybridization:

5'-CGCGGATCCTAAGGAGGTGATCATATGAACTT TAAAAAATACGAAGAA-3' (195-152) (SEQ ID NO:19)

The reverse primer was designed to hybridize to *Staphylococcus warneri* DNA at the 3' end of the swaIR gene. It contained a XhoI restriction site to facilitate cloning.

5'- GCATCTCGAGTTAAATTGAGTTGTCATTAGA AT-3' (195-153) (SEQ ID NO:20)

These two primers were used to amplify the swaIR gene from *Staphylococcus warneri* genomic DNA by combining:

30 µl 10× Taq PCR Buffer (containing 1.5 mM Mg++)
30 µl 2 mm dNTPs
0.75 µl (450 ng) *Staphylococcus warneri* genomic DNA
3 µl primer 195-152 (225 ng)
3 µl primer 195-153 (225 ng)
227.5 µl dH$_2$O
3 µl (0.3 units) Deep Vent® polymerase
3 µl Taq DNA polymerase (15 units)

and amplifying for 25 cycles at 95° C. for 30 seconds, 50° C. for 1 minute and 72° C. for 2 minutes. The amplification product was purified using the Promega Wizard PCR Prep Kit. 1 µg of pHKT7 vector and the remaining PCR product (~1 ug) were both digested with 20 units of BamHI and 20 units of XhoI, supplemented with 0.1 mg/ml BSA in 1× NEB BamHI buffer in a 50 µl reaction that was incubated at 37° C. for one hour. The digests were run on a 1% low melting-point NuSieve agarose gel in TAE buffer. The PCR and vector DNA bands (681 and 3500 bp respectively) were cut out and the gel slices were incubated at 65° C. for 10 minutes. The temperature was reduced to 40° C. and the gel slices were treated with β-Agarase. The ligation of pHKT7 and swaIR was performed by combining the following at 37° C.:

9.0 µl prepared pHKT7 (100 ng)
7 µl endonuclease PCR product (70 ng)
5 µl 10× T4 DNA Ligase Buffer
2 µl T4 DNA Ligase (800 units)
27 ul dH$_2$O The reaction was incubated at 37° C. for one hour. Ten µl of the ligation reaction was transformed into *E. coli* strain ER2566 previously modified with the SwaI methylase gene. Transformants were analyzed and all contained the swaIR gene. This plasmid construct, pHKT7-swaIR, was selected for producing the SwaI endonuclease. The *E. coli* strain which contains both pHKT7-swaIR and pHKUV5-swaIM plasmids was designated as NEB#1183. The yield of recombinant SwaI from strain NEB#1183 was approximately 2.0×10$^5$ units/gram of cells.

3. Producing the recombinant SwaI restriction endonuclease from *E. coli* ER2566 NEB#1183

*E. coli* ER2566 NEB#1183 was grown to mid-log phase in a fermenter containing L-broth medium with ampicillin (100 µg/ml) and chloramphenicol (50 µg/ml). The culture was induced by the addition of IPTG to a final concentration of 0.4 mM and allowed to continue growing for 16 hours. The cells were harvested by centrifugation and may be stored at −70° C. or used immediately.

Purification of the SwaI restriction endonuclease from *E. coli* NEB#1183 can be accomplished by a combination of standard protein purification techniques, such as affinity-chromatography or ion-exchange chromatography, as outlined in Example 1 above. The SwaI restriction endonuclease obtained from this purification is substantially pure and free of non-specific endonuclease and exonuclease contamination.

A sample of the *E. coli* ER2566 NEB#1183 which contains both pHKUV5-swaIM and pHKT7-swaIR plasmids has been deposited under the terms and conditions of the Budapest Treaty with the American Type Culture Collection on Apr. 23, 1999 and received ATCC Accession No. 207227.

What is claimed is:

1. Isolated DNA encoding the SwaI restriction endonuclease, wherein the isolated DNA is obtainable from ATCC No. 207227.

2. A vector which comprises the isolated DNA of claim 1.

3. A host cell transformed by the vector of claim 2.

4. A method of producing SwaI restriction endonuclease comprising culturing a host cell transformed with the vector of claim 2 under conditions suitable for expression of said endonuclease.

* * * * *

UNITED STATES PATENT AND TRADEMARK OFFICE
CERTIFICATE OF CORRECTION

PATENT NO. : 6,245,545 B1　　　　　　　　　　　　　　　　　Page 1 of 1
DATED : June 12, 2001
INVENTOR(S) : Huimin Kong, Lauren S. Higgins, Michael A. Dalton It is certified that error appears in the above-identified patent and that said Letters Patent is hereby corrected as shown below:

Column 2,
Line 5, replace "78 1503-1507" with -- 78:1503-1507 --

Column 2,
Line 48, replace "(1991),)." with -- (1991)). --

Column 4,
Line 13, after "in" delete "the"

Column 5,
Line 11, after "interfere" insert -- with --
Line 67, replace "refridg-" with -- refrig- --

Column 6,
Line 42, replace "a" with -- an --

Column 8,
Line 42, replace "refridgerator" with -- refrigerator --

Column 10,
Line 41, replace "Staphylococcus warneri" with -- *Staphylococcus warneri* --

Column 11,
Line 36, replace "a" with -- an --
Line 53, replace "2  mm " " with -- 2mM --

Signed and Sealed this

Twelfth Day of March, 2002

*Attest:*

*Attesting Officer*

JAMES E. ROGAN
*Director of the United States Patent and Trademark Office*

SEQUENCE LISTING

<160> NUMBER OF SEQ ID NOS: 20

<210> SEQ ID NO 1
<211> LENGTH: 681
<212> TYPE: DNA
<213> ORGANISM: Staphylococcus warneri

```
<220> FEATURE:
<221> NAME/KEY: CDS
<222> LOCATION: (1)..(678)

<400> SEQUENCE: 1 atg aac ttt aaa aaa tac gaa gaa aat cta gta gca tct att gaa gaa      48
Met Asn Phe Lys Lys Tyr Glu Glu Asn Leu Val Ala Ser Ile Glu Glu
 1               5                  10                  15 gtt att caa cgc att ata gat gat aaa cat aga cct aat att ata ggt      96
Val Ile Gln Arg Ile Ile Asp Asp Lys His Arg Pro Asn Ile Ile Gly
             20                  25                  30 aaa aca aga gta ggc gct gaa gtt agc gat tac tta gaa gat gaa ttt     144
Lys Thr Arg Val Gly Ala Glu Val Ser Asp Tyr Leu Glu Asp Glu Phe
         35                  40                  45 gta aag tat ata tct agt gga aag agt agt agc tta tat gat gct caa     192
Val Lys Tyr Ile Ser Ser Gly Lys Ser Ser Ser Leu Tyr Asp Ala Gln
     50                  55                  60 gga gca cct aaa gaa aag act aaa aac cca tgg gac gca aga tgt aaa     240
Gly Ala Pro Lys Glu Lys Thr Lys Asn Pro Trp Asp Ala Arg Cys Lys
 65                  70                  75                  80 ttt aag ttt atg gat aga gaa gaa gaa att tgg att gat ttt aaa gca     288
Phe Lys Phe Met Asp Arg Glu Glu Glu Ile Trp Ile Asp Phe Lys Ala
                 85                  90                  95 ttt aaa ata act aac atg gat agt aat ccg gat att gga act cct aat     336
Phe Lys Ile Thr Asn Met Asp Ser Asn Pro Asp Ile Gly Thr Pro Asn
            100                 105                 110 aaa ata gtt aag ttc att cat gaa ggg aat ttt tat tta gtt ttt gta     384
Lys Ile Val Lys Phe Ile His Glu Gly Asn Phe Tyr Leu Val Phe Val
        115                 120                 125 ctt gtg tat tat gaa agt aaa caa gat ggt gtt gaa ttt gta aaa tat     432
Leu Val Tyr Tyr Glu Ser Lys Gln Asp Gly Val Glu Phe Val Lys Tyr
    130                 135                 140 aat aat gat tat aaa aaa gtt tac tta tta aaa gat gtt aat gaa tca     480
Asn Asn Asp Tyr Lys Lys Val Tyr Leu Leu Lys Asp Val Asn Glu Ser
145                 150                 155                 160 ttt aga att aat cca aaa cca cag atg caa gtt aat att gca gca gaa     528
Phe Arg Ile Asn Pro Lys Pro Gln Met Gln Val Asn Ile Ala Ala Glu
                165                 170                 175 ccc aca ttt aga act aga gaa gaa ttt att cat ttc ttt gtt aaa aaa     576
Pro Thr Phe Arg Thr Arg Glu Glu Phe Ile His Phe Phe Val Lys Lys
            180                 185                 190 tgg aaa gag tca ttt gaa aga cag ata aaa tct tta gaa aaa aaa gaa     624
Trp Lys Glu Ser Phe Glu Arg Gln Ile Lys Ser Leu Glu Lys Lys Glu
        195                 200                 205 ata atg tta aaa gat cta gaa gat aaa ttg aaa aat tct aat gac aac     672
Ile Met Leu Lys Asp Leu Glu Asp Lys Leu Lys Asn Ser Asn Asp Asn
    210                 215                 220 tca att taa                                                          681
Ser Ile
225

<210> SEQ ID NO 2
<211> LENGTH: 226
<212> TYPE: PRT
<213> ORGANISM: Staphylococcus warneri

<400> SEQUENCE: 2

Met Asn Phe Lys Lys Tyr Glu Glu Asn Leu Val Ala Ser Ile Glu Glu
 1               5                  10                  15

Val Ile Gln Arg Ile Ile Asp Asp Lys His Arg Pro Asn Ile Ile Gly
             20                  25                  30
```

```
Lys Thr Arg Val Gly Ala Glu Val Ser Asp Tyr Leu Glu Asp Glu Phe
        35                  40                  45

Val Lys Tyr Ile Ser Ser Gly Lys Ser Ser Ser Leu Tyr Asp Ala Gln
    50                  55                  60

Gly Ala Pro Lys Glu Lys Thr Lys Asn Pro Trp Asp Ala Arg Cys Lys
65                  70                  75                  80

Phe Lys Phe Met Asp Arg Glu Glu Ile Trp Ile Asp Phe Lys Ala
                85                  90                  95

Phe Lys Ile Thr Asn Met Asp Ser Asn Pro Asp Ile Gly Thr Pro Asn
                100                 105                 110

Lys Ile Val Lys Phe Ile His Glu Gly Asn Phe Tyr Leu Val Phe Val
                115                 120                 125

Leu Val Tyr Tyr Glu Ser Lys Gln Asp Gly Val Glu Phe Val Lys Tyr
    130                 135                 140

Asn Asn Asp Tyr Lys Lys Val Tyr Leu Leu Lys Asp Val Asn Glu Ser
145                 150                 155                 160

Phe Arg Ile Asn Pro Lys Pro Gln Met Gln Val Asn Ile Ala Ala Glu
                165                 170                 175

Pro Thr Phe Arg Thr Arg Glu Glu Phe Ile His Phe Val Lys Lys
                180                 185                 190

Trp Lys Glu Ser Phe Glu Arg Gln Ile Lys Ser Leu Glu Lys Lys Glu
    195                 200                 205

Ile Met Leu Lys Asp Leu Glu Asp Lys Leu Lys Asn Ser Asn Asp Asn
        210                 215                 220

Ser Ile
225

<210> SEQ ID NO 3
<211> LENGTH: 1857
<212> TYPE: DNA
<213> ORGANISM: Staphylococcus warneri
<220> FEATURE:
<221> NAME/KEY: CDS
<222> LOCATION: (1)..(1854)

<400> SEQUENCE: 3 atg aaa aat tat aat tta ata gac tta tat tca tta tat ttc gaa att        48
Met Lys Asn Tyr Asn Leu Ile Asp Leu Tyr Ser Leu Tyr Phe Glu Ile
  1               5                  10                  15 gac aaa gta aaa cta aga gat atg ttt cag aat ata tca att gaa gta        96
Asp Lys Val Lys Leu Arg Asp Met Phe Gln Asn Ile Ser Ile Glu Val
                 20                  25                  30 aaa ctt aat gag gct caa gtt gat gaa ata ctc aaa cta gat ata ttt       144
Lys Leu Asn Glu Ala Gln Val Asp Glu Ile Leu Lys Leu Asp Ile Phe
             35                  40                  45 aca ttt tat aat gaa atc aat cta tta ata agc aaa aca att gag act       192
Thr Phe Tyr Asn Glu Ile Asn Leu Leu Ile Ser Lys Thr Ile Glu Thr
         50                  55                  60 tct aat aga aaa gat aat gga ata tat ttc act caa gat ttt aat gtt       240
Ser Asn Arg Lys Asp Asn Gly Ile Tyr Phe Thr Gln Asp Phe Asn Val
 65                  70                  75                  80 ata aaa agg ata ata caa tta tct att gat aaa ata cct aat act tta       288
Ile Lys Arg Ile Ile Gln Leu Ser Ile Asp Lys Ile Pro Asn Thr Leu
                 85                  90                  95 tta aca aag aaa aaa gta tta gat cca gct tgt ggt acg ggt ata ttt       336
Leu Thr Lys Lys Lys Val Leu Asp Pro Ala Cys Gly Thr Gly Ile Phe
                100                 105                 110
```

```
                                                              -continued tca ata gct ttc ata cat gaa att ttc aac aga caa att agt aaa aat        384
Ser Ile Ala Phe Ile His Glu Ile Phe Asn Arg Gln Ile Ser Lys Asn
        115                 120                 125 tct ata gtt gat ttt ata aat aac tac tta gta aat ata gat gtt tca        432
Ser Ile Val Asp Phe Ile Asn Asn Tyr Leu Val Asn Ile Asp Val Ser
    130                 135                 140 aat gaa atg att aat ttt act aag atc aat att ctt act atg atg tat        480
Asn Glu Met Ile Asn Phe Thr Lys Ile Asn Ile Leu Thr Met Met Tyr
145                 150                 155                 160 tat cta tat aat gac ata agt atc ttt gat aaa gta aaa cct aat ata        528
Tyr Leu Tyr Asn Asp Ile Ser Ile Phe Asp Lys Val Lys Pro Asn Ile
                165                 170                 175 tat gct ata gat ttt gtt tat caa gaa aaa cac aaa gaa ttt aat tta        576
Tyr Ala Ile Asp Phe Val Tyr Gln Glu Lys His Lys Glu Phe Asn Leu
            180                 185                 190 ttt aat tat ttt aat tct caa aat caa aat ttt att aat gat aat ttt        624
Phe Asn Tyr Phe Asn Ser Gln Asn Gln Asn Phe Ile Asn Asp Asn Phe
        195                 200                 205 gag aat ttt gat ata gtt ata ggc aat cct cca tac gta tcc ttg tat        672
Glu Asn Phe Asp Ile Val Ile Gly Asn Pro Pro Tyr Val Ser Leu Tyr
210                 215                 220 gga aga cga gcc ata aat aag agt gaa gat aaa aga caa ttt tta ata        720
Gly Arg Arg Ala Ile Asn Lys Ser Glu Asp Lys Arg Gln Phe Leu Ile
225                 230                 235                 240 cga aat tat gat ttt ata cct aaa aac gta aaa aat gga aaa ttt aat        768
Arg Asn Tyr Asp Phe Ile Pro Lys Asn Val Lys Asn Gly Lys Phe Asn
                245                 250                 255 tac aca atg ttt ttt att gaa aat ggt tta caa cta cta aaa aag aat        816
Tyr Thr Met Phe Phe Ile Glu Asn Gly Leu Gln Leu Leu Lys Lys Asn
            260                 265                 270 ggt act tta aca ttt att gta gat ata act tta ctt gaa agt tct ttt        864
Gly Thr Leu Thr Phe Ile Val Asp Ile Thr Leu Leu Glu Ser Ser Phe
        275                 280                 285 gaa tca att aga aaa tat att tta gaa act gcc att ata aag caa ctt        912
Glu Ser Ile Arg Lys Tyr Ile Leu Glu Thr Ala Ile Ile Lys Gln Leu
290                 295                 300 gat atc aat tta aaa gct ttt agt gat gta gtt agt gga caa ata atc        960
Asp Ile Asn Leu Lys Ala Phe Ser Asp Val Val Ser Gly Gln Ile Ile
305                 310                 315                 320 att tct ctt tta aaa aat gca tcc aac aaa gaa gct att gta agt atc       1008
Ile Ser Leu Leu Lys Asn Ala Ser Asn Lys Glu Ala Ile Val Ser Ile
                325                 330                 335 aaa gat tgg caa aat aat aac aca att caa att aat caa gat ata tgg       1056
Lys Asp Trp Gln Asn Asn Asn Thr Ile Gln Ile Asn Gln Asp Ile Trp
            340                 345                 350 ttg cat gat aaa ttt tat cgt ttt aat att agc gat aag aaa ata aat       1104
Leu His Asp Lys Phe Tyr Arg Phe Asn Ile Ser Asp Lys Lys Ile Asn
        355                 360                 365 tca att tta gag aaa gtt tac aat aaa tca gat gaa ctt caa tat tat       1152
Ser Ile Leu Glu Lys Val Tyr Asn Lys Ser Asp Glu Leu Gln Tyr Tyr
370                 375                 380 ttt cct aag aaa gag tta cgt act tct act atg tta ttg aat atg gaa       1200
Phe Pro Lys Lys Glu Leu Arg Thr Ser Thr Met Leu Leu Asn Met Glu
385                 390                 395                 400 tct tcc ttc gtt aaa gat tat aaa cca gaa acg gat ttt cac gta atg       1248
Ser Ser Phe Val Lys Asp Tyr Lys Pro Glu Thr Asp Phe His Val Met
                405                 410                 415 cct tat tat aag gga gcc aaa aat tta tct ttt cca ttt caa aat atg       1296
Pro Tyr Tyr Lys Gly Ala Lys Asn Leu Ser Phe Pro Phe Gln Asn Met
            420                 425                 430
```

```
cat tca aat cac tat ttt ata tac gat aca gct tta caa aaa aag att    1344
His Ser Asn His Tyr Phe Ile Tyr Asp Thr Ala Leu Gln Lys Lys Ile
        435                 440                 445 aat gat tca ctt cat gaa gaa tta tta aaa aaa gga ata aaa aat aaa    1392
Asn Asp Ser Leu His Glu Glu Leu Leu Lys Lys Gly Ile Lys Asn Lys
450                 455                 460 aaa aga att ggt tta ggt aac tta gag gtg ttt aaa aac ccg aaa ctt    1440
Lys Arg Ile Gly Leu Gly Asn Leu Glu Val Phe Lys Asn Pro Lys Leu
465                 470                 475                 480 ttt att aga caa tct gct aat aag ctt ata gca acc ttt gat ggt aaa    1488
Phe Ile Arg Gln Ser Ala Asn Lys Leu Ile Ala Thr Phe Asp Gly Lys
                485                 490                 495 atg tca gct tca aat aat agt tta tat atc tta agt aaa gca act aac    1536
Met Ser Ala Ser Asn Asn Ser Leu Tyr Ile Leu Ser Lys Ala Thr Asn
        500                 505                 510 gat ata aaa gat ata aat atg cta aaa att aca tgt gct caa cta aat    1584
Asp Ile Lys Asp Ile Asn Met Leu Lys Ile Thr Cys Ala Gln Leu Asn
        515                 520                 525 tct gaa tta tta aca ttt att gca ctt aca aat aga att atc cga aaa    1632
Ser Glu Leu Leu Thr Phe Ile Ala Leu Thr Asn Arg Ile Ile Arg Lys
530                 535                 540 gct gaa ggc aaa caa cct caa att aaa ttg tca gat tta aaa aca att    1680
Ala Glu Gly Lys Gln Pro Gln Ile Lys Leu Ser Asp Leu Lys Thr Ile
545                 550                 555                 560 cca cta tgt ttt aat gaa gag att aat tct aag tta tta att ttt gca    1728
Pro Leu Cys Phe Asn Glu Glu Ile Asn Ser Lys Leu Leu Ile Phe Ala
                565                 570                 575 gaa aat gct act aaa aaa aat aat gaa tta gaa agt tct tta gaa aaa    1776
Glu Asn Ala Thr Lys Lys Asn Asn Glu Leu Glu Ser Ser Leu Glu Lys
                580                 585                 590 atc aat caa att att tat aaa tat tat gat att aac ggt gaa gaa gta    1824
Ile Asn Gln Ile Ile Tyr Lys Tyr Tyr Asp Ile Asn Gly Glu Glu Val
        595                 600                 605 gaa ttt att aaa aac tat att aat tca aat tag                        1857
Glu Phe Ile Lys Asn Tyr Ile Asn Ser Asn
    610                 615

<210> SEQ ID NO 4
<211> LENGTH: 618
<212> TYPE: PRT
<213> ORGANISM: Staphylococcus warneri

<400> SEQUENCE: 4

Met Lys Asn Tyr Asn Leu Ile Asp Leu Tyr Ser Leu Tyr Phe Glu Ile
 1               5                  10                  15

Asp Lys Val Lys Leu Arg Asp Met Phe Gln Asn Ile Ser Ile Glu Val
            20                  25                  30

Lys Leu Asn Glu Ala Gln Val Asp Glu Ile Leu Lys Leu Asp Ile Phe
        35                  40                  45

Thr Phe Tyr Asn Glu Ile Asn Leu Leu Ile Ser Lys Thr Ile Glu Thr
    50                  55                  60

Ser Asn Arg Lys Asp Asn Gly Ile Tyr Phe Thr Gln Asp Phe Asn Val
65                  70                  75                  80

Ile Lys Arg Ile Ile Gln Leu Ser Ile Asp Lys Ile Pro Asn Thr Leu
                85                  90                  95

Leu Thr Lys Lys Lys Val Leu Asp Pro Ala Cys Gly Thr Gly Ile Phe
            100                 105                 110

Ser Ile Ala Phe Ile His Glu Ile Phe Asn Arg Gln Ile Ser Lys Asn
```

-continued

```
                115                 120                 125
Ser Ile Val Asp Phe Ile Asn Asn Tyr Leu Val Asn Ile Asp Val Ser
    130                 135                 140
Asn Glu Met Ile Asn Phe Thr Lys Ile Asn Ile Leu Thr Met Met Tyr
145                 150                 155                 160
Tyr Leu Tyr Asn Asp Ile Ser Ile Phe Asp Lys Val Lys Pro Asn Ile
                165                 170                 175
Tyr Ala Ile Asp Phe Val Tyr Gln Glu Lys His Lys Glu Phe Asn Leu
                180                 185                 190
Phe Asn Tyr Phe Asn Ser Gln Asn Gln Asn Phe Ile Asn Asp Asn Phe
            195                 200                 205
Glu Asn Phe Asp Ile Val Ile Gly Asn Pro Pro Tyr Val Ser Leu Tyr
    210                 215                 220
Gly Arg Arg Ala Ile Asn Lys Ser Glu Asp Lys Arg Gln Phe Leu Ile
225                 230                 235                 240
Arg Asn Tyr Asp Phe Ile Pro Lys Asn Val Lys Asn Gly Lys Phe Asn
                245                 250                 255
Tyr Thr Met Phe Phe Ile Glu Asn Gly Leu Gln Leu Leu Lys Lys Asn
                260                 265                 270
Gly Thr Leu Thr Phe Ile Val Asp Ile Thr Leu Leu Glu Ser Ser Phe
            275                 280                 285
Glu Ser Ile Arg Lys Tyr Ile Leu Glu Thr Ala Ile Ile Lys Gln Leu
    290                 295                 300
Asp Ile Asn Leu Lys Ala Phe Ser Asp Val Val Ser Gly Gln Ile Ile
305                 310                 315                 320
Ile Ser Leu Leu Lys Asn Ala Ser Asn Lys Glu Ala Ile Val Ser Ile
                325                 330                 335
Lys Asp Trp Gln Asn Asn Asn Thr Ile Gln Ile Asn Gln Asp Ile Trp
                340                 345                 350
Leu His Asp Lys Phe Tyr Arg Phe Asn Ile Ser Asp Lys Lys Ile Asn
            355                 360                 365
Ser Ile Leu Glu Lys Val Tyr Asn Lys Ser Asp Glu Leu Gln Tyr Tyr
    370                 375                 380
Phe Pro Lys Lys Glu Leu Arg Thr Ser Thr Met Leu Leu Asn Met Glu
385                 390                 395                 400
Ser Ser Phe Val Lys Asp Tyr Lys Pro Glu Thr Asp Phe His Val Met
                405                 410                 415
Pro Tyr Tyr Lys Gly Ala Lys Asn Leu Ser Phe Pro Phe Gln Asn Met
                420                 425                 430
His Ser Asn His Tyr Phe Ile Tyr Asp Thr Ala Leu Gln Lys Lys Ile
            435                 440                 445
Asn Asp Ser Leu His Glu Glu Leu Leu Lys Gly Ile Lys Asn Lys
    450                 455                 460
Lys Arg Ile Gly Leu Gly Asn Leu Glu Val Phe Lys Asn Pro Lys Leu
465                 470                 475                 480
Phe Ile Arg Gln Ser Ala Asn Lys Leu Ile Ala Thr Phe Asp Gly Lys
                485                 490                 495
Met Ser Ala Ser Asn Asn Ser Leu Tyr Ile Leu Ser Lys Ala Thr Asn
                500                 505                 510
Asp Ile Lys Asp Ile Asn Met Leu Lys Ile Thr Cys Ala Gln Leu Asn
            515                 520                 525
Ser Glu Leu Leu Thr Phe Ile Ala Leu Thr Asn Arg Ile Ile Arg Lys
    530                 535                 540
```

-continued

```
Ala Glu Gly Lys Gln Pro Gln Ile Lys Leu Ser Asp Leu Lys Thr Ile
545                 550                 555                 560

Pro Leu Cys Phe Asn Glu Glu Ile Asn Ser Lys Leu Leu Ile Phe Ala
            565                 570                 575

Glu Asn Ala Thr Lys Lys Asn Asn Glu Leu Glu Ser Ser Leu Glu Lys
            580                 585                 590

Ile Asn Gln Ile Ile Tyr Lys Tyr Tyr Asp Ile Asn Gly Glu Glu Val
            595                 600                 605

Glu Phe Ile Lys Asn Tyr Ile Asn Ser Asn
            610                 615

<210> SEQ ID NO 5
<211> LENGTH: 31
<212> TYPE: PRT
<213> ORGANISM: Staphylococcus warneri

<400> SEQUENCE: 5

Met Asn Phe Lys Lys Tyr Glu Glu Asn Leu Val Ala Ser Ile Glu Glu
 1               5                  10                  15

Val Ile Gln Xaa Ile Ile Asp Asp Lys Xaa Xaa Pro Asn Ile Ile
            20                  25                  30

<210> SEQ ID NO 6
<211> LENGTH: 7
<212> TYPE: PRT
<213> ORGANISM: Staphylococcus warneri

<400> SEQUENCE: 6

Asn Phe Lys Lys Tyr Glu Glu
 1               5

<210> SEQ ID NO 7
<211> LENGTH: 21
<212> TYPE: DNA
<213> ORGANISM: Staphylococcus warneri

<400> SEQUENCE: 7
aayttyaara artaygarga g                                          21

<210> SEQ ID NO 8
<211> LENGTH: 15
<212> TYPE: DNA
<213> ORGANISM: Staphylococcus warneri

<400> SEQUENCE: 8
ngtyttnccd atdat                                                 15

<210> SEQ ID NO 9
<211> LENGTH: 21
<212> TYPE: DNA
<213> ORGANISM: Staphylococcus warneri

<400> SEQUENCE: 9
ttcttcaata gatgctacta g                                          21

<210> SEQ ID NO 10
<211> LENGTH: 20
<212> TYPE: DNA
<213> ORGANISM: Staphylococcus warneri

<400> SEQUENCE: 10
```

-continued gttattcaac gcattataga                                          20

<210> SEQ ID NO 11
<211> LENGTH: 22
<212> TYPE: DNA
<213> ORGANISM: Staphylococcus warneri

<400> SEQUENCE: 11
cacatttaga actagagaag aa                                       22

<210> SEQ ID NO 12
<211> LENGTH: 23
<212> TYPE: DNA
<213> ORGANISM: Staphylococcus warneri

<400> SEQUENCE: 12
ggttctgctg caatattaac ttg                                      23

<210> SEQ ID NO 13
<211> LENGTH: 24
<212> TYPE: DNA
<213> ORGANISM: Staphylococcus warneri

<400> SEQUENCE: 13
taatctttaa cgaaggaaga ttcc                                     24

<210> SEQ ID NO 14
<211> LENGTH: 22
<212> TYPE: DNA
<213> ORGANISM: Staphylococcus warneri

<400> SEQUENCE: 14
taaaccagaa acggattttc ac                                       22

<210> SEQ ID NO 15
<211> LENGTH: 25
<212> TYPE: DNA
<213> ORGANISM: Staphylococcus warneri

<400> SEQUENCE: 15
ggtataaaat cataatttcg tatta                                    25

<210> SEQ ID NO 16
<211> LENGTH: 22
<212> TYPE: DNA
<213> ORGANISM: Staphylococcus warneri

<400> SEQUENCE: 16
taaaaacgta aaaatggaa aa                                        22

<210> SEQ ID NO 17
<211> LENGTH: 50
<212> TYPE: DNA
<213> ORGANISM: Staphylococcus warneri

<400> SEQUENCE: 17
aaaactgcag ataaggaggt gatcgtatga aaaattataa tttaatagac          50

<210> SEQ ID NO 18
<211> LENGTH: 42
<212> TYPE: DNA
<213> ORGANISM: Staphylococcus warneri

<400> SEQUENCE: 18

```
cgcggatcca tttaaatcta atttgaatta atatagtttt ta                    42

<210> SEQ ID NO 19
<211> LENGTH: 48
<212> TYPE: DNA
<213> ORGANISM: Staphylococcus warneri

<400> SEQUENCE: 19
cgcggatcct aaggaggtga tcatatgaac tttaaaaaat acgaagaa              48

<210> SEQ ID NO 20
<211> LENGTH: 33
<212> TYPE: DNA
<213> ORGANISM: Staphylococcus warneri

<400> SEQUENCE: 20
gcatctcgag ttaaattgag ttgtcattag aat                              33
```